United States Patent [19]

Kay

[11] Patent Number: 5,263,947

[45] Date of Patent: Nov. 23, 1993

[54] EXTERNAL INCONTINENCE DEVICE

[75] Inventor: Dennis M. Kay, Tampa, Fla.

[73] Assignee: BioDerm, Inc., Tampa, Fla.

[21] Appl. No.: 747,376

[22] Filed: Aug. 20, 1991

[51] Int. Cl.⁵ .............................................. A61F 5/44
[52] U.S. Cl. .................................. 604/331; 128/761;
604/329; 604/351; 604/349; 604/353
[58] Field of Search ............... 128/760, 761, 767, 842,
128/844; 604/326, 337, 349, 351, 353;
4/144.1-144.3

[56] References Cited

U.S. PATENT DOCUMENTS

| | | | |
|---|---|---|---|
| 3,559,651 | 2/1971 | Moss | 604/349 |
| 4,484,914 | 11/1984 | Brown | 604/180 |
| 4,534,762 | 8/1985 | Heyer | 604/180 |
| 4,600,001 | 7/1986 | Gilman | 128/156 |
| 4,626,250 | 12/1986 | Schneider | 604/349 |
| 4,759,354 | 7/1988 | Quarfoot | 128/156 |
| 4,767,411 | 8/1988 | Edmunds | 604/180 |
| 4,790,834 | 12/1988 | Austin | 604/349 |
| 4,901,375 | 2/1990 | Dahlgren | 4/144.3 |
| 4,904,247 | 2/1990 | Therriault et al. | 604/304 |
| 4,913,138 | 4/1990 | Yoshida et al. | 128/155 |
| 4,915,102 | 4/1990 | Kwiatek et al. | 128/156 |
| 5,087,252 | 2/1992 | Denard | 604/349 |

Primary Examiner—Randall L. Green
Assistant Examiner—Rob Clarke
Attorney, Agent, or Firm—Foley & Lardner

[57] ABSTRACT

An external incontinence device which reduces or eliminates maceration, skin irritation, microbial skin infiltration and infection, and urinary tract infection associated with conventional urinary catheters and incontinence devices is provided. The device comprises a housing having an outlet conduit, a plurality of leaves made of a thin, vapor permeable film connected to the housing, a vapor permeable adhesive on the interior surface of the leaves, a microbial-barrier layer provided on an inner surface of the housing and a barrier disc provided on the inner surface of the housing. The vapor-permeable leaves allow water vapor to evaporate from the underlying skin surface, thus eliminating maceration. In addition, a U-shaped release backing on each leaf allows the leaves to be applied to the skin surface in a wrinkle-free manner. The microbial-barrier layer comprises an antimicrobial agent to prevent microbial infiltration into the urethral meatus, thus reducing or eliminating the incidence of urinary tract infection. The barrier disc comprises various medically active substances and forms an occlusive adhesive seal with the para-meatal surface.

29 Claims, 4 Drawing Sheets

EXTERNAL INCONTINENCE DEVICE

BACKGROUND OF THE INVENTION

The present invention relates to an external incontinence device for medical use. Urinary incontinence, a common medical problem, is currently treated with condom catheters, invasive catheters, incontinence pads and diapers.

There are several problems associated with the current treatments, most prominent of which is a high incidence of infections. The incidence of urinary tract infections with indwelling invasive urinary catheters is well described in current medical literature. The presence of an invasive catheter in the urethra is thought to facilitate the infiltration of microorganisms. Microorganisms at the catheter entrance site ascend the catheter through the urethra into the urinary tract, thus resulting in infections. The conventional condom catheter is essentially a bag connected to a tube. This sheath is usually attached to the penis by a circumferential adhesive band. Often the attachment is inadequate and the condom catheter falls off or leaks. In other cases, the circumferential adhesive band results in irritation or even strangulation of the penis. The condom catheter design presents no barrier to the infiltration of microorganisms into the urethra. Inside the bag, the moist environment is ideal for microorganism growth. Microorganisms growing in the moist environment in the bag can enter the urethra and proceed into the urinary tract causing urinary tract infections.

Incontinence pads or diapers, whether used on male or female patients, also contribute to the onset and severity of infections because the excreted urine and/or feces contained in these devices are excellent media for bacterial growth. Such bacteria can enter the urethra because in long term care facilities personnel are often unable to change patients' diapers as frequently as recommended by good medical practice.

The second problem associated with current incontinence treatments is particularly related to the condom catheter. The conventional condom catheter causes skin maceration and irritation. The epidermis is composed of dead cells which protect the underlying living dermis cells from physical and chemical irritation and from microbial invasion. Maceration refers to the problems associated with prolonged exposure of the epidermis to moisture. When epidermal cells are exposed to moisture for a sufficient period of time, they absorb water, swell, and slough off, thus exposing the physiologically active dermal layer to whatever chemical or microbial entities are present in the immediate environment.

Maceration occurs not only when the skin is exposed to water from external sources but also when moisture is trapped against the skin surface by a water-impermeable membrane. Skin continually emits water, particularly in the genital area. If the emitted water is trapped against the skin surface by a water-impermeable membrane and is not able to evaporate, then maceration occurs.

If maceration proceeds unabated, an inflammation of cellular and connective tissue caused by the failure of the epidermis, often occurs. This inflammation is often accompanied or followed by microbial invasion, causing a cellulitis or tissue infection. Microbial invasion causes further tissue inflammation and destruction. In severe cases of cellulitis, extensive tissue destruction, necrosis or gangrene ensues, necessitating removal of the gangrenous tissues or the entire affected limb. Clearly, maintaining skin dryness is necessary to prevent the onset of maceration and further degenerative states.

The conventional condom catheter functions as a bag of moisture surrounding the penis. The condom catheter does not allow the necessary evaporation of moisture from the skin surface. Not only do the walls of the condom trap the emitted moisture against the skin surface, but urination also adds to the moisture trapped inside the condom and contributes chemical irritants, such as urea, to the enclosed area. Thus, conventional condom catheters cause maceration and skin irritation.

The maceration and skin irritation caused by condom catheters make them physically uncomfortable, and patients routinely remove them, either deliberately or inadvertently while sleeping. In addition, macerated tissue is moist and loose. Adhesive, therefore, does not adhere well to macerated skin. Thus, adding a simple adhesive to the condom catheter does not help, because the condom catheter becomes loose or falls off of the patient due to maceration under the adhesive.

SUMMARY OF THE INVENTION

It is therefore an object of the present invention to reduce or eliminate microbial infiltration and the resulting infections associated with the use of conventional urinary catheters, incontinence pads and diapers.

Yet another object of the present invention is to reduce or prevent maceration and skin irritation due to condom catheter use.

An additional object of the present invention is to provide a more comfortable external incontinence device, thus increasing patient compliance.

Another object of the present invention is to provide an external incontinence device that can be worn for up to seven days.

In satisfying these and other objects, there has been provided, in accordance with one aspect of the present invention, an external incontinence device comprising a housing which presents an outer surface and an inner surface wherein the inner surface is adapted for attachment to the para-meatal surface surrounding a urethral meatus. The housing comprises an outlet conduit for fluid drainage which has an internal and an external end wherein the internal end penetrates through the inner surface of the housing. A means for holding the housing over the urethral meatus so that the internal end of the outlet conduit communicates freely with the meatus is also provided, comprising a plurality of leaves connected to the housing wherein each leaf of the plurality has an interior surface and an exterior surface and the leaves are comprised of a vapor permeable film such that evaporation of water vapor from the skin surrounding the para-meatal surface can occur and maceration is avoided.

In accordance with other aspects of the invention, a vapor permeable adhesive layer is provided on the interior surface of each of the leaves, such that each leaf can be secured on the para-meatal surface. A microbial-barrier layer is provided on the inner surface of the housing, the layer comprising a medically active substance which prevents microbial infiltration into the housing.

The device further comprises a barrier disc which is provided on the inner surface of the housing and which surrounds the internal end of the conduit, the barrier disc being disposed to surround the urethral meatus to provide an occlusive mechanical seal against contaminants. In a preferred embodiment of the invention, the barrier disc comprises a hydrocolloid which absorbs water and urine. Additionally, the barrier disc can comprise a hydrocolloid formulated to adhere to the para-meatal surface and surround either a male urethral opening or a female urethral opening to occlusively seal against contaminants. The barrier disc can further comprise an adhesive layer to increase the secureness of the attachment to the para-meatal surface.

Additional holding means of the device comprise a plurality of U-shaped release backings which communicate with the vapor permeable adhesive on the leaves, such that the leaves are capable of wrinkle-free application to the para-meatal surface, and appropriate location and secure attachment of the device is maintained. The release backings of the inventions comprise a release portion which communicates with the vapor permeable adhesive layer and a pull tab which communicates with the release portion and extends away from the interior surfaces of the leaf, such that the application of force to the pull tab in a direction away from the housing causes a smooth transverse removal of the release portion from the leaf, whereby the leaf is applied to the para-meatal surface in a wrinkle-free manner.

Further in accordance with the objects of the invention, the edges of the attachment leaves are provided in shapes which have no corners and wherein the edges of the leaves are tapered away from the housing. The vapor permeable film is provided in thicknesses from 0.3 to 1.5 mils and is impermeable to microbes and other contaminants. Preferred materials are the polyurethane films which are configured in leaves which overlap one another to provide sufficient attachment surface to securely attach the device to the wearer.

In accordance with still other objects of the invention, in a preferred female-adapted embodiment, the holding means further comprises a nonadhesive means for attaching the device to the para-meatal surface which is a plurality of retaining straps connected to a plurality of attachment points on the housing wherein the retaining straps are provided with a plurality of adjustment buckles for changing the length and fit of the retaining straps to further assure the maintenance of the device in the proper position with respect to the urethral meatus.

Still further in accordance with the objects of the invention, the adhesive in the microbial-barrier layer is formulated to be moisture compatible and the outlet conduit comprises an anti-microbial or an antiseptic coating provided on the inside surface of the outlet conduit such that microbial infiltration through the outlet conduit is attenuated. The outlet conduit is provided with an integral adaptor on the external end, such that attachment of the outlet conduit to various tubing connectors is permitted.

Still in accordance with the objects of the invention, the barrier disc is further provided with a protective release backing, preferably configured to be U-shaped, which covers the barrier disc prior to application of the device to the para-meatal surface. In addition, the barrier disc further comprises an anti-microbial or antiseptic agent provided throughout the substance of the barrier disc as an integral component thereof such that microbial infiltration into the urethral meatus is attenuated.

Other objects, features and advantages of the present invention will become apparent from the following detailed description. It should be understood, however, that the detailed description and the specific examples, while indicating preferred embodiments of the invention, are given by way of illustration only. The detailed description herein will suggest changes and modifications within the spirit and scope of the invention that may become apparent to those skilled in the art. These changes and modifications are considered within the scope of the subject invention.

BRIEF DESCRIPTION OF THE DRAWINGS

In order that the invention may be more readily understood, and so that further features thereof may be appreciated, the invention will now be described by way of example with reference to the accompanying drawings, in which FIGS. 1-4 relate to the male-adapted embodiment of the invention and FIGS. 5-14 relate to the female-adapted embodiment of the invention and in which.

DETAILED DESCRIPTION OF THE PREFERRED EMBODIMENTS

The present invention uses tapered leaves of an adhesive coated, vapor permeable film to affix to the patient's para-meatal skin an anatomically contoured housing with an outlet conduit. The outlet conduit which carries urine away from the genital area does not enter the urethral meatus but instead is held in close approximation to the urethral meatus by the device's adhesive means. The vapor permeable film is divided into more than one piece, thus forming the leaves.

The urethral meatus is the external opening of the urethra in a male or female patient. In the male, the urethral meatus is typically found at the end of the penis. In the female, the urethral meatus is typically found anterior to the vaginal introitus (opening). The para-meatal surface is that surface which comprises the urethral meatus and surrounding skin or mucosal tissue near the urethral meatus in either the male or the female.

Gases, particularly water vapor, can pass through the film leaves from the skin into the surrounding atmosphere. However, the film is impermeable to microbes, thus preventing microbes from passing through the film from the surrounding environment and becoming trapped against the skin surface. The film is also impermeable to other contaminants. Such contaminants include microbes, urine, feces, pus, sloughed off skin, hair, and/or any other substance which may present the problems of chemical irritation or microbial infiltration.

The leaves have a vapor permeable adhesive, for example, an acrylic medical skin adhesive which is known in the art is applied, in a continuous or discontinuous layer, on their interior surface. The adhesive or interior surface of the leaves attaches to the surface of the skin. The leaves preferably are comprised of 0.3 to 2.0 mil polyurethane film. The thinness and constituency of the film allow moisture to evaporate from the skin surface through the leaves, thus maintaining a dry epidermal layer and reducing or eliminating skin irritation and maceration noted with the use of condom catheters and other conventional incontinence devices.

The tapered shape of the leaves minimizes the area covered by the film while providing stable immobilization of the device. In accordance with a preferred embodiment of the present invention, the leaves overlap at the housing and become gradually narrower as they proceed away from the housing, that is, the leaves are tapered. The leaves are wider and overlapping at the housing attachment site because secure attachment around the housing is critical. Therefore, through the use of vapor permeable film leaves with a skin compatible vapor permeable adhesive and a smaller surface area than that covered by conventional condom catheters, the present invention eliminates the skin irritation and maceration caused by condom catheters, diapers and incontinence pads.

The maceration and skin irritation associated with conventional condom catheters and other devices make the devices physically uncomfortable. By reducing maceration and skin irritation, patient comfort is increased, and patient compliance increases correspondingly.

In addition, the present invention reduces or eliminates the incidence of infection from condom catheter use by providing a zone of asepsis around the urethral meatus. A zone of asepsis is created by preventing microbial infiltration. Several elements of the present invention resist microbial infiltration of the urethral meatus.

A barrier disk layer is provided on the skin application surface of the housing. This barrier disc functions as a microbial-barrier layer, containing either an antiseptic agent, for example, povidone iodine or benzalkonium chloride, or an antimicrobial agent to inhibit bacterial growth. In a preferred embodiment of the present invention, the barrier disc layer includes an adhesive, for example, a hydrocolloid, to help hold the housing in close approximation to the urethral meatus. A preferred hydrocolloid is composed of a synthetic nitrile adhesive (e.g. Vistanex(®), Exxon Corp) 70%, pectin (e.g. Benecel(®), Hercules Chemical, Inc.) 20% and povidone iodine (Betadine(®), Purdue-Frederick, Inc.) 10%.

The hydrocolloid and antiseptic disc layer provide several infection control and skin protective functions of the subject invention. The hydrocolloid disc forms an occlusive seal or mechanical barrier around the urethral meatus, thus protecting the entrance of the urinary tract from exposure to extraneous bacteria. The occlusive nature of the disc also prevents exposure of the para-meatal skin surface to the macerating effects of excreted urine. The hydrocolloid disc functions as an effective moisture barrier and seal. The excreted urine passes through the central opening of the disc, into the device housing and thence into an attached urinary drainage tube. Therefore, the remainder of the para-meatal surface is never exposed to the excreted urine, in distinction to condom catheters.

The barrier disc is preferably made of a hydrocolloid which absorbs skin perspiration and prevents accumulation of excess moisture on the skin surface. Therefore, the barrier disc helps to prevent maceration and skin irritation, as well as preventing microbial infiltration.

The adhesive coated, vapor permeable leaves are made of a conformable film, enabling the leaves to assume the shape of the underlying para-meatal skin surface. The leaves are applied to the skin surface through removal of a novel U-shaped release backing on each leaf. These U-shaped release backings protect the vapor-permeable adhesive prior to application of the device. The U-shaped release backing allows each leaf to be applied to the skin surface in a wrinkle-free manner, from a point most proximal to the plastic housing to a point more distal from the plastic housing, with the device already in place on the para-meatal surface.

With respect to the release backing and pull tab components of the invention, "U-shaped" means that the pull tab is substantially parallel to the corresponding release backing and the two are connected at ends by an adhesive or by a weld so that the pull tab and the release backing approximate the arms of the letter "U" with the bottom of the "U" being the connection of the two pieces. This connection is of relatively small dimension when compared to the lengths of the pull tab and backing so that the arms of the "U" are relatively long. Alternatively, the pull tab and release backing can be of one piece folded back on itself to also form, substantially, a "U" shape with the fold therin being the bottom of the "U".

The U-shaped release backing preferably is made of a piece of plastic or plastic-coated paper which is folded approximately in halves. One portion of the backing, the release portion, is located over the adhesive on the leaves, such that the adhesive layer is enclosed between the backing and the interior surface of the leaf. The other portion of the backing is folded back away from the leaf and comprises a pull tab. The pull tabs are of sufficient stiffness to provide that the application of force to each pull tab in a direction away from the housing causes a smooth transverse removal of the backing from the corresponding leaf. In a preferred embodiment, the pull tab portion of the backing has a greater modulus of rigidity than the release portion. The differential in rigidity facilitates the smooth and easy removal of the backing from the corresponding leaf. The pull tabs can be of various lengths, for example, in one preferred embodiment, the pull tab portion of the backing is longer than the release portion. The conformability of the leaf film and the design of the backings facilitate a smooth, wrinkle-free application of the leaves to the para-meatal surface. The resulting wrinkle-free layer of film on the skin surface ensures the maintenance of the proper location of the device proximate to the urethral meatus and a more secure adhesive attachment of the device.

The barrier disc creates a mechanical barrier to moisture and microbial infiltration because it is pressed securely against the skin surface by the leaves. In a preferred embodiment, the barrier disc is made of a hydrocolloid with adhesive properties that adheres intimately to the skin, creating a stronger mechanical barrier than that created by pressure alone. By preventing moisture and microbial infiltration, the incidence of urinary tract infections, skin irritation and urine leakage associated with conventional condom catheter, invasive catheter, incontinence pad and diaper use are reduced or eliminated.

Similar problems exist with respect to female incontinence. Due to a shorter urethra, female patients are particularly subjected to the infections associated with wearing invasive catheters, incontinence pads and diapers. Diapers and incontinence pads also cause skin irritation and maceration which potentially results in skin ulceration and infection, especially for bed-bound female patients.

The female-adapted urinary incontinence device functions in essentially the same way as the male-adapted device to solve these problems. The female-adapted device housing is contoured to accommodate the different shape of the female para-meatal surfaces and vaginal introitus. The barrier disc in the female-adapted device functions in the same way as it does in the male-adapted device, but it is also configured to conform to the female para-meatal surfaces and the vaginal introitus.

In one embodiment of the female device, additional nonadhesive attachment means are provided. In a preferred embodiment, the attachment means consists of several retaining straps attached to the exterior surface of the housing and to a retaining belt around the patient's waist. The retaining straps preferably have adjustment buckles to allow adjustment of the length of the retaining straps to fit differently sized patients.

Patients, male or female, can wear a device of the present invention for prolonged periods, for example, up to seven days. In contrast, current condom catheter, diaper, and incontinence pad designs require that such devices be changed every day to reduce the risk of infection, skin maceration, irritation, urine leakage and to maintain an effective attachment. Presently, the cost of replacing the condom catheters and other incontinence devices daily and the lack of properly supervised personnel in nursing homes and hospitals result in catheters being worn longer than recommended by the manufacturers. The effectiveness of the catheters, thus, is reduced further and the risk of infection is increased. The ability to effectively wear the present invention for prolonged periods without infection will decrease the cost of treatment and reduce the personnel time required to change catheters or make diaper and bedding changes in long term care facilities.

The external incontinence device is applied to a patient's skin using aseptic technique and clean exam gloves. In a male patient, the foreskin is retracted and the urethral meatus, penile tip and corona are cleansed using gauze or cotton swabs moistened with a standard skin cleanser or antiseptic, such as povidone iodine or benzalkonium chloride. A small amount of skin preparation for adhesive attachment, such as tincture of Benzoin may be applied to the penile tip surrounding the urethral meatus to facilitate improved adhesive attachment of the hydrocolloid disc and adhesive leaves to the penile tip. The protective release backing for the barrier disc is removed from the device and the housing is mounted on the penis with the outlet conduit centered over the urethral meatus. The remaining exposed portions of the penile tip are thoroughly dried. The U-shaped release backings are removed individually from each of the leaves by placing pressure on each leaf near the housing with one hand and pulling on the corresponding pull tab with the other hand, causing each leaf to adhere to the penis from the penile tip toward the corona and securing the device in place. The integral adaptor of the device housing is then attached to the appropriate tubing connector.

A similar attachment procedure is followed with respect to the female-adapted device except that the attachment leaves are applied as the labia minora surfaces are spread slightly to assure intimate contact of the adhesive surfaces with the para-meatal skin. In addition, in the preferred embodiment having attachment straps, the straps are adjusted to provide sufficient tension on the housing that it remains in the desired position with respect to the urethral meatus.

The present invention can be more fully appreciated with reference to the above-noted figures and to the following detailed description of those figures. In connection with the foregoing figures, like reference numerals will refer to like portions thereof.

Figure 1:
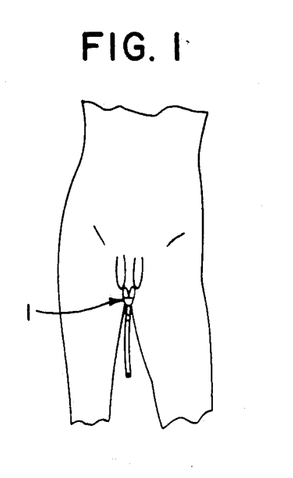
FIG. 1 is a perspective view of a male-adapted external incontinence device in use.

FIG. 1 shows an external incontinence device in use on a male patient. FIGS. 1-4 illustrate the male-adapted embodiment of the device.

Figure 2:
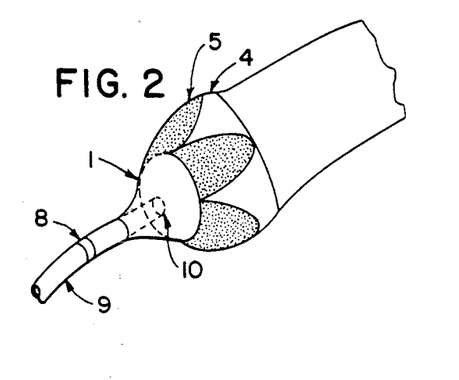
FIG. 2 is a close-up perspective view of the male-adapted device in use.
Figure 3:
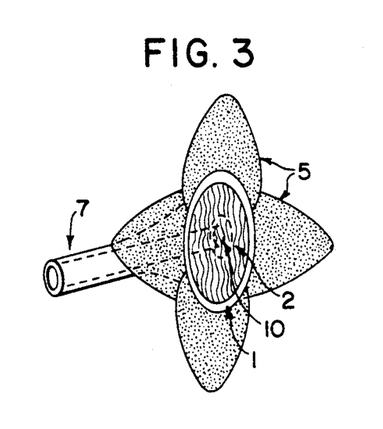
FIG. 3 is an oblique top view showing the attachment surface of the male-adapted device.
Figure 4:
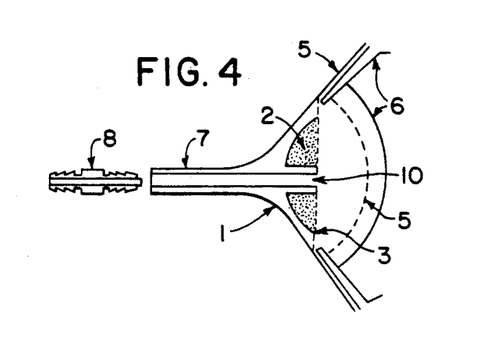
FIG. 4 is a cross-sectional side view of the device illustrating the barrier disc and release backings.

With reference to FIGS. 2-4, an external incontinence device is shown attached to a penis 4. A housing 1 having an outlet conduit 10 attaches over the end of the penis 4. The outlet conduit 10 breaches an inner surface of the housing 1, and urine is carried away from the penis 4 through the outlet conduit 10. An integral adaptor 7 is located on the housing 1 to allow attachment to various tubing connectors 8, such as a standard "Christmas Tree" connector.

A plurality of leaves 5 are attached to the housing 1. The leaves 5 adhere to the para-meatal surface of the penis 4, as shown. The leaves 5 have a vapor permeable adhesive (not shown) on their skin attachment surface. The leaves 5 are shown in FIG. 3 without U-shaped release backing 6, (which is shown in FIG. 4). FIG. 3 shows an oblique end view of the male-adapted external incontinence device illustrating the skin attachment surface of the leaves 5 covered with the vapor permeable adhesive layer (not shown). A barrier disc 2 is also shown disposed on the inner surface of housing 1 surrounding the outlet conduit 10 of the housing 1.

FIG. 4 shows, in cross section, a preferred shape of the barrier disc 2. A protective release backing 3 adheres to the barrier disc 2 to be removed before application of the device to the skin. In addition, a U-shaped, adhesive release backing 6 is shown covering the skin attachment surface of the leaves 5.

FIGS. 2 and 4 also illustrate a tubing connector 8, a standard "Christmas Tree" connector shown positioned to be attached to the integral adaptor 7 of FIG. 4 and shown linking to urinary drainage tube 9 and the device in FIG. 2.

Figure 5:
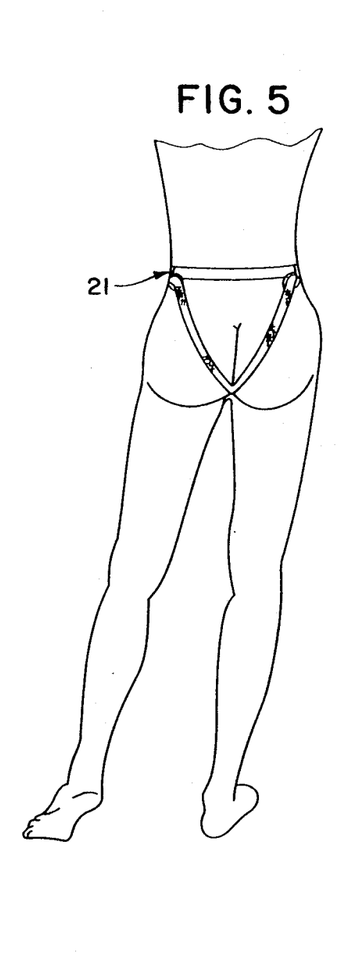
FIG. 5 is a perspective view of the device in use on a female patient shown from the rear of the patient.
Figure 6:
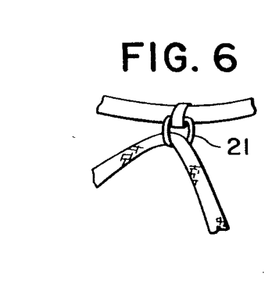
FIG. 6 is a close-up view of the ring attachment.
Figure 7:
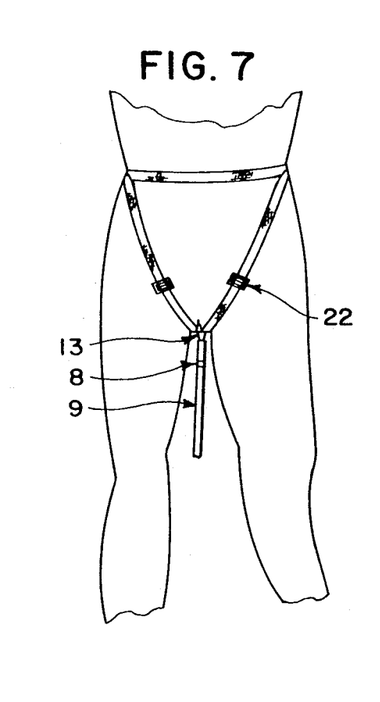
FIG. 7 is a perspective view of the device in use shown from the front of a female patient.
Figure 8:
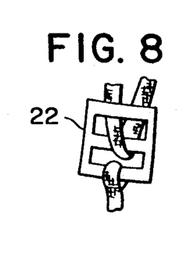
FIG. 8 is a close-up view of the retaining strap adjustment buckle.
Figure 9:
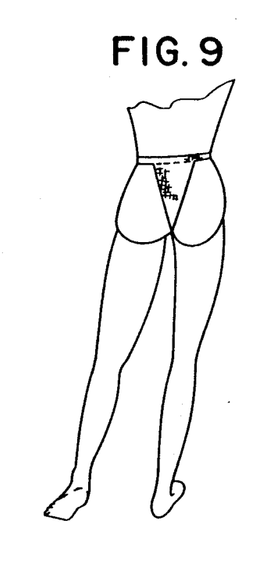
FIG. 9 is a perspective view of an alternative embodiment of the device in use.

FIGS. 5-14 illustrate the female-adapted embodiment of the device. FIGS. 5-7, 9 and 12 show the device in use on a female patient. FIGS. 5 and 9 illustrate alternative embodiments for the retaining straps 23. FIG. 7 illustrates the retaining straps from the front of the patient.

FIG. 6 illustrates the attachment of the retaining straps 23 to a belt 21 worn around the patient's waist, as shown in FIG. 5. The retaining straps 23 are attached to the belt 21 with a ring (not numbered).

FIG. 8 illustrates a retaining strap adjustment buckle 22. The location of the buckle 22 on the retaining straps 23 is shown in FIG. 7. The adjustment buckle 22 allows adjustment of the length of the retaining straps 23 to fit differently sized patients.

Figure 10:
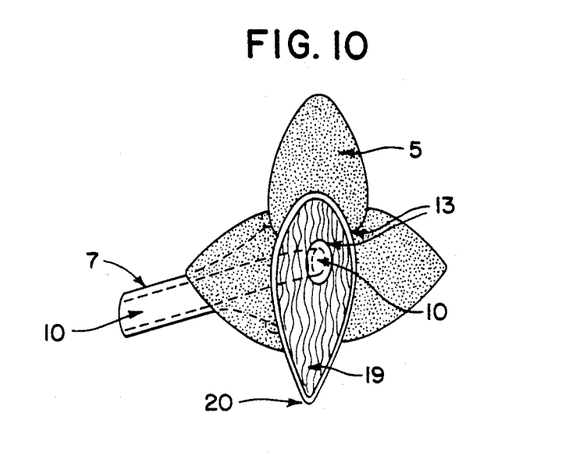
FIG. 10 is an oblique side view showing the attachment surface of the female-adapted device.
Figure 12:
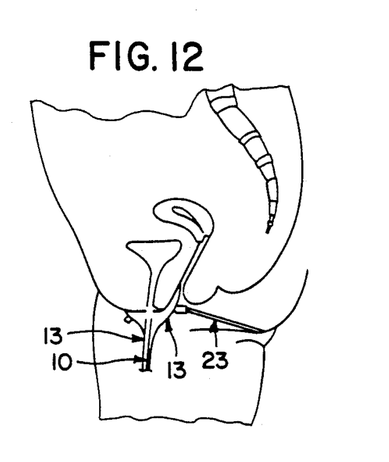
FIG. 12 is a side view of the female-adapted device in use.

FIG. 10 shows an a oblique side view of the female embodiment of the external incontinence device. A housing 13 having an outlet conduit 10 attaches over the urethral meatus with the tapered curved lip 20 of the housing 13 inserted into the vaginal introitus of the patient, as shown in FIG. 12. The outlet conduit 10 breaches an inner surface (not shown) of the housing 13, and urine is carried away from the urethral meatus through the outlet conduit 10. An integral adaptor 7 is located on the housing 13 to allow attachment to various tubing connectors 8, such as a standard "Christmas Tree" connector.

Figure 13:
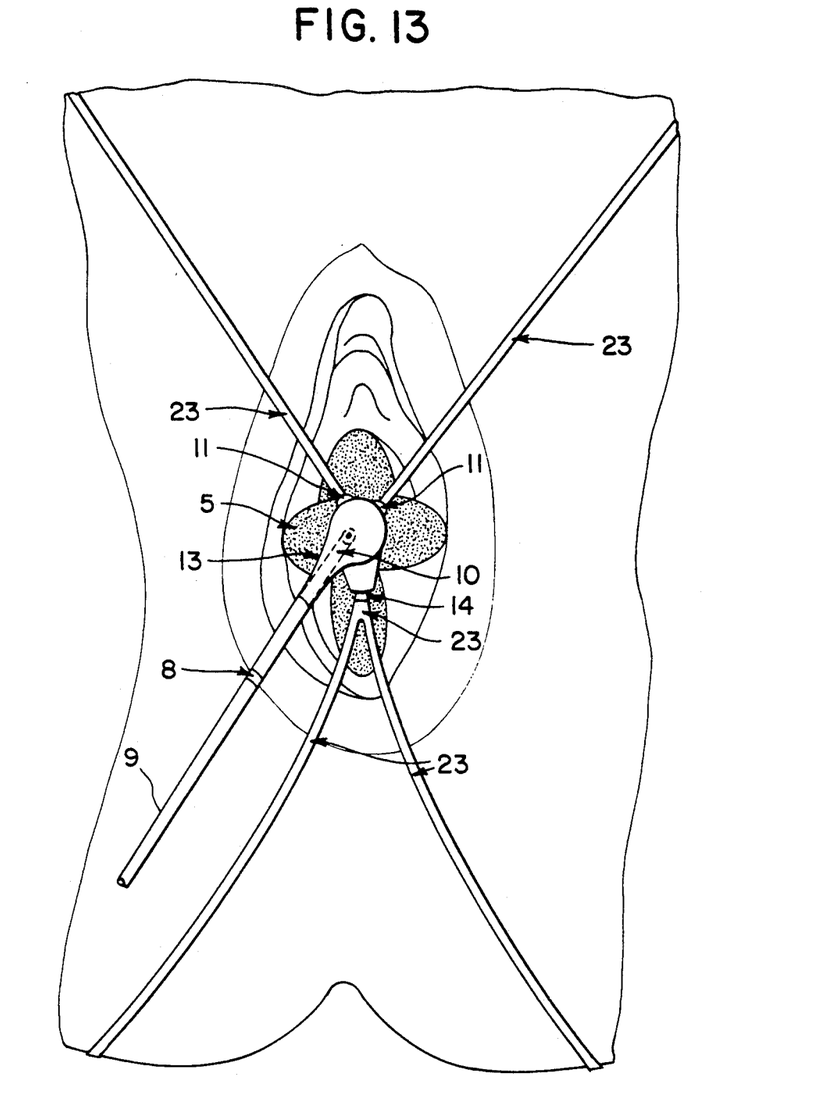
FIG. 13 is a bottom view of the female-adapted device in use.
Figure 14:
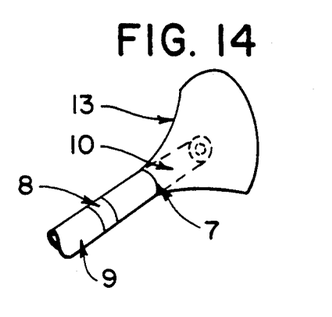
FIG. 14 is a perspective view of the female-adapted device.

A plurality of leaves 5 are attached to the housing 13. The leaves 5 adhere to the skin surrounding the urethral meatus, as shown in FIG. 13. The leaves 5 have a vapor permeable adhesive (not shown) on their skin attachment surface. The leaves 5 are shown without release backings 6 in FIG. 10 and with the release backings 6 in FIG. 11. A barrier disc 19 is also shown on the inner surface of the housing 13.

Figure 11:
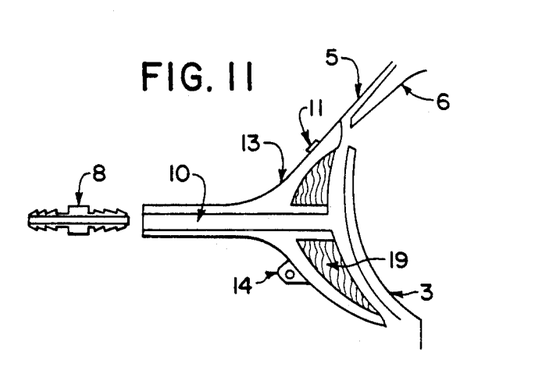
FIG. 11 is a cross-sectional side view of the female-adapted device illustrating the barrier disc and the release backings.

FIG. 11 shows a preferred shape of the barrier disc 19. A protective U-shaped release backing 3 adheres to the barrier disc 19 before application of the device to the skin. In addition, a U-shaped, adhesive release backing 6 is shown covering the skin attachment surface (not shown) of the leaves 5. The retaining strap attachment points 11 and 14 are also shown.

FIG. 11 illustrates a tubing connector 8, such as a standard "Christmas Tree" connector. The tubing connector 8 is shown attached to the integral adaptor 7 and to a urinary drainage tube 9 in FIG. 14.

With the exception of the barrier disc, the elements of the present invention are manufactured by standard manufacturing procedures and from materials well-known in medical device manufacturing.

From the foregoing description, it is evident that there are a number of changes, adaptations and modifications of the subject invention that are within the province of those persons having ordinary skill in the pertinent art. The inventor intends that all such variations, not departing from the spirit of the subject invention, be considered as within the scope of the subject invention as limited only by the appended claims.

What is claimed is:

1. An external incontinence device comprising:
    (A) a housing which presents an outer surface and an inner surface wherein
        (1) said inner surface is adapted for attachment to a para-meatal surface surrounding a urethral meatus,
        (2) said housing comprises an outlet conduit for fluid drainage, and
        (3) said outlet conduit has an internal end and an external end, said internal end penetrating through said inner surface;
    (B) means for holding said housing over said urethral meatus so that said internal end of said outlet conduit communicates freely with said meatus, said means comprising
        (1) a plurality of leaves connected to said housing, wherein (a) each leaf of said leaves has an interior surface and an exterior surface and (b) said leaves are comprised of a vapor permeable film such that evaporation of water vapor from the leaf adhesion site of the skin surrounding said urethral meatus can occur and maceration is avoided, and
        (2) a vapor-permeable adhesive layer provided on said interior surface of each said leaf, such that each said leaf can be secured on said para-meatal surface; and
    (C) a microbial-barrier layer, provided on said inner surface of said housing, said layer comprising a medically active substance which prevents microbial infiltration into said housing,
    wherein said internal end of said outlet conduit does not extend beyond the longest reach of said plurality of leaves.

2. The device of claim 1, further comprising a barrier disc which is provided on said inner surface of said housing and which surrounds said internal end of said conduit, said barrier disc disposed to surround said urethral meatus to provide an occlusive mechanical seal against contaminants.

3. The device of claim 2, wherein said barrier disc comprises a hydrocolloid which absorbs water and urine.

4. The device of claim 3, wherein said hydrocolloid is formulated to adhere to said para-meatal surface.

5. The device of claim 4, wherein said barrier disc is annular.

6. The device of claim 5, wherein said housing is specifically adapted for attachment to a male para-meatal surface.

7. The device of claim 5, wherein said housing is specifically adapted for attachment to a female para-meatal surface.

8. The device of claim 5, wherein said barrier disc further comprises an adhesive.

9. The device of claim 8, wherein said holding means further comprises a plurality of U-shaped release backings which communicate with said vapor permeable adhesive on each of said leaves, such that said leaves are capable of wrinkle-free application to said para-meatal surface, and appropriate location and secure attachment of said device is maintained.

10. The device of claim 9, wherein each said release backing comprises (i) a release portion which communicates with said vapor permeable adhesive layer and (ii) a pull tab which communicates with said release portion and extends away from said interior surface of said leaf, such that the application of force to said pull tab in a direction away from said housing causes a smooth transverse removal of said release portion from said leaf, whereby said leaf is applied to said para-meatal surface in a wrinkle-free manner.

11. The device of claim 10, wherein the edges of each of said leaves have no corners.

12. The device of claim 11, wherein the edges of each of said leaves are tapered away from said housing.

13. The device of claim 12, wherein said vapor permeable film is from 0.3 to 2.0 mil thick.

14. The device of claim 13, wherein each of said leaves overlap one another.

15. The device of claim 14, wherein said vapor permeable film is microbe impermeable.

16. The device of claim 15, wherein said vapor permeable film is polyurethane.

17. The device of claim 2, wherein said holding means further comprises a nonadhesive means for attaching said device to said para-meatal surface.

18. The device of claim 17, wherein said nonadhesive attaching means further comprises a plurality of retaining straps connected to said housing.

19. The device of claim 18, wherein said housing further comprises a plurality of attachment points for use with said nonadhesive attaching means.

20. The device of claim 19, wherein said retaining straps further comprise a plurality of adjustment buckles for changing the length of said retaining straps.

21. The device of claim 8, wherein said adhesive in said microbial-barrier layer is moisture compatible.

22. The device of claim 2, wherein said barrier disc comprises an antimicrobial substance.

23. The device of claim 2, wherein said barrier disc comprises an antiseptic coating provided on the skin attachment surface of said barrier disc.

24. The device of claim 2, wherein said outlet conduit further comprises an antimicrobial coating provided on the inside surface of said outlet.

25. The device of claim 2, wherein said outlet conduit further comprises an antiseptic coating provided on the inside surface of said outlet conduit.

26. The device of claim 2, wherein said outlet conduit comprises an integral adaptor provided on said external end, such that attachment of said outlet conduit to various tubing connectors is permitted.

27. The device of claim 2, wherein said barrier disc further comprises a protective release backing which covers said barrier disc prior to application of said device to said para-meatal surface.

28. The device of claim 25, wherein said protective release backing is U-shaped.

29. An external incontinence device comprising:
(A) a housing which presents an outer surface and an inner surface wherein
  (1) said inner surface is adapted for attachment to a para-meatal surface surrounding a urethral meatus,
  (2) said housing comprises an outlet conduit for fluid drainage, and
  (3) said outlet conduit has an internal end and an external end, said internal end penetrating through said inner surface;
(B) means for holding said housing over said urethral meatus so that said internal end of said outlet conduit communicates freely with said meatus, said means comprising
  (1) a plurality of leaves connected to said housing, wherein (a) each of said leaves has an interior surface and an exterior surface and (b) said leaves are comprised of a vapor permeable film such that evaporation of water vapor from the leaf adhesion site of the skin surrounding said urethral meatus can occur and maceration is avoided, and
  (2) a vapor-permeable adhesive layer provided on said interior surface of each said leaf, such that each said leaf can be secured on said para-meatal surface; and
(C) a microbial-barrier layer, provided on said inner surface of said housing, said layer comprising a disc disposed to surround said urethral meatus to provide an occlusive mechanical seal against microbial infiltration into said housing,
wherein said internal end of said outlet conduit does not extend beyond the longest reach of said plurality of leaves.

* * * * *